(12) United States Patent
Ressel

(10) Patent No.: US 10,501,485 B2
(45) Date of Patent: Dec. 10, 2019

(54) PROCESS FOR PRODUCING PHOSPHINATES

(71) Applicant: BASF SE, Ludwigshafen am Rhein (DE)

(72) Inventor: Hans-Joachim Ressel, Hattersheim (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/763,398

(22) PCT Filed: Sep. 26, 2016

(86) PCT No.: PCT/EP2016/072786
§ 371 (c)(1),
(2) Date: Mar. 26, 2018

(87) PCT Pub. No.: WO2017/055193
PCT Pub. Date: Apr. 6, 2017

(65) Prior Publication Data
US 2018/0265529 A1 Sep. 20, 2018

(30) Foreign Application Priority Data
Sep. 29, 2015 (EP) .................................... 15187469

(51) Int. Cl.
*C07F 9/32* (2006.01)
*C07F 9/40* (2006.01)

(52) U.S. Cl.
CPC .......... *C07F 9/3211* (2013.01); *C07F 9/3223* (2013.01); *C07F 9/4075* (2013.01)

(58) Field of Classification Search
CPC ............................. C07F 9/3211; C07F 9/3223
See application file for complete search history.

(56) References Cited

U.S. PATENT DOCUMENTS

| | | | |
|---|---|---|---|
| 3,914,345 A | 10/1975 | Kleiner et al. |
| 4,168,963 A | 9/1979 | Rupp et al. |
| 4,474,711 A | 10/1984 | Keliner et al. |
| 4,485,052 A | 11/1984 | Kleiner et al. |
| 4,521,348 A | 6/1985 | Finke et al. |
| 4,599,207 A | 7/1986 | Lachhein et al. |
| 5,128,495 A | 7/1992 | Scheffel et al. |
| 5,166,385 A | 11/1992 | Scheffel et al. |
| 6,359,162 B1 | 3/2002 | Willms |

FOREIGN PATENT DOCUMENTS

| | | |
|---|---|---|
| GB | 1461376 A | 1/1977 |
| GB | 1490835 A | 11/1977 |

OTHER PUBLICATIONS

International Search Report of International Patent Application No. PCT/EP2015/072786 dated Nov. 21, 2016.
Jablonkai et al., "T3P assisted esterification and amidation of phosphinic acids" Tetrahedron. (2014) vol. 70: 8280-8285.
Daugherty et al., "Nuclear Magnetic Resonance Study of the Hydrolysis of Diethyl Methylphosphonite" Applied Spectroscopy. (1968) vol. 22, No. 2: 95-98.
Hoffmann et al., "Organic Phosphorus Compounds" J. Am. Chem. Soc. (1958) vol. 80: 5937-5940.
Karanewsky et al., "(Phosphinyloxy)acyl Amino ACid Inhibitors of Angiotensin Converting Enzyme (ACE)". J. Med. Chem. (1988) vol. 31: 204-212.
Kabachnik et al., "Esters of Unsaturated Phosphorus Acids" J. of General Chem. of the USSR. (1962) vol. 32: 3288-3296.
Ebetino et al., "A stereoselective process for the preparation of novel phosphonoalkylphosphinates" J. Organomet. Chem. (1997) vol. 529: 135-142.
Petnehazy et al., "Convenient One Pot Synthesis of Phosphonites and H-Phosphinates" Syntheteic Communications. (2003) vol. 33: 1665-1674.

*Primary Examiner* — Shawquia Jackson
(74) *Attorney, Agent, or Firm* — McBee Moore Woodward & Vanik IP, LLC

(57) ABSTRACT

The present invention relates primarily to a process for producing particular phosphinates (phosphonous acid monoesters) and use thereof for producing biologically active substances which may be used in the pharmaceutical or agrochemical sector, preferably for producing phosphorus-containing amino acids.

19 Claims, No Drawings

PROCESS FOR PRODUCING PHOSPHINATES

CROSS-REFERENCE TO RELATED APPLICATIONS

This application is a National Stage entry of International Application No. PCT/EP2016/072786, filed Sep. 26, 2016, which claims priority to European Patent Application No. 15187469.0, filed Sep. 29, 2015.

BACKGROUND

Field

The present invention relates primarily to a process for producing phosphinates (phosphonous acid monoesters) of the defined formula (I) below and use thereof for producing biologically active substances which may be used in the pharmaceutical or agrochemical sector, preferably for producing phosphorus-containing amino acids.

Description of Related Art

Phosphinates (phosphonous acid monoesters), alkyl phosphinates for example (alkylphosphonous acid monoesters), are valuable intermediates in various industrial fields, in particular for producing biologically active substances which can be employed in the pharmaceutical or agrochemical sector.

U.S. Pat. No. 4,168,963, for example, describes a wide variety of phosphorus-containing herbicidally active compounds, among which in particular phosphinothricin (2-amino-4-[hydroxy(methyl)phosphinoyl]butanoic acid; common name: glufosinate, referred to hereinbelow as glufosinate) and the salts thereof have attained commercial importance in the agrochemical sector.

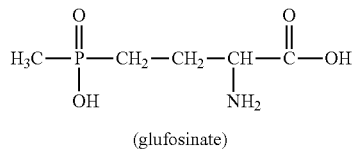

(glufosinate)

Methods for producing intermediates for the synthesis of such phosphorus-containing herbicidally active compounds, in particular of glufosinate, are described in U.S. Pat. Nos. 4,521,348, 4,599,207 and 6,359,162B1 for example.

The production of monoalkyl phosphinates is known to those skilled in the art and may be effected according to processes known from the literature, for example in accordance with U.S. Pat. Nos. 3,914,345; 4,474,711 or 5,128,495).

The production of monoalkyl phosphinates starting from particular halophosphorus compounds is described, for example, in U.S. Pat. No. 4,485,052, GB 1461 376 and GB 1 490 835.

The production of dialkyl alkylphosphonites is described, for example, in U.S. Pat. No. 5,166,385.

Furthermore, saponification reactions of certain dialkyl alkylphosphonites to give alkyl phosphinic acids or monoesters thereof are known, as described for example in Applied Spectroscopy 1968, 22, 95-98, J. Med. Chem. 1988, 31, 204-212, J. of General Chem. of the USSR 1962, 32, 3288-3296, Synthetic Communications 2003, 33, 1665-1674 and J. Organomet. Chem. 1997, 529, 135-142.

J. Am. Chem. Soc. 1958, 80, 5937-5940 describes the transesterification of certain dialkyl alkylphosphonites.

The processes from the prior art for producing alkyl phosphinates (alkylphosphonous acid monoesters) still have disadvantages however, such as insufficient purities and/or yields of alkyl phosphinates (alkylphosphonous acid monoesters), an excessive fraction of co-products or by-products, excessively complicated purification or isolation of the alkyl phosphinates (alkylphosphonous acid monoesters) and/or reaction conditions that are excessively difficult in terms of process or plant technology.

Alkylphosphonous acid mono-$C_1$-$C_3$-esters are preferably not used on an industrial scale due to their low stability and their hazard potential. In the large scale synthesis of glufosinate ammonium, therefore, butyl methylphosphinate is an important intermediate.

SUMMARY

The object of the present invention, therefore, was to find a process for producing phosphinates (phosphonous acid monoesters), particularly alkyl phosphinates (alkylphosphonous acid monoesters), which affords the phosphinates (phosphonous acid monoesters) in improved yields and/or gives rise to a lower fraction of co-products or by-products, and in addition preferably enables an improved reaction regime, for example, in relation to aspects relevant to safety, environment and/or quality, and are thus preferably also suitable for performance on an industrial scale.

The process according to the invention described below achieves this object.

The present invention provides a process for producing phosphinates (phosphonous acid monoesters) of formula (I)

characterized in that a compound of formula (II)

is reacted with a compound of formula (III)

wherein in each case:
$R^1$ represents ($C_1$-$C_{12}$)-alkyl, ($C_1$-$C_{12}$)-haloalkyl, ($C_6$-$C_{10}$)-aryl, ($C_6$-$C_{10}$)-haloaryl, ($C_7$-$C_{10}$)-aralkyl, ($C_7$-$C_{10}$)-haloaralkyl, ($C_4$-$C_{10}$)-cycloalkyl or ($C_4$-$C_{10}$)-halocycloalkyl,
$R^2$ represents ($C_3$-$C_{12}$)-alkyl, ($C_3$-$C_{12}$)-haloalkyl, ($C_6$-$C_{10}$)-aryl, ($C_6$-$C_{10}$)-haloaryl, ($C_7$-$C_{10}$)-aralkyl, ($C_7$-$C_{10}$)-haloaralkyl, ($C_4$-$C_{10}$)-cycloalkyl or ($C_4$-$C_{10}$)-halocycloalkyl,
$R^3$ and $R^4$ each independently of one another represent methyl or ethyl,
in the presence of an acidic catalyst and in the presence of water.

DETAILED DESCRIPTION OF A PREFERRED EMBODIMENT

The desired phosphinates (phosphonous acid monoesters) of formula (I) are obtained in excellent yield and in very high purity with the process according to the invention by the reaction of the compound of formula (II) with an alcohol of formula (III), at the same time in the presence of a minimum amount of water and in the presence of an acidic catalyst.

In the process according to the invention, partial hydrolysis and transesterification of the compounds of formula (II) takes place in situ, preferably in a one-pot reaction. In the process according to the invention, particularly in one of the configurations of the process according to the invention designated as preferred or as particularly preferred, the phosphinates (phosphonous acid monoesters) of formula (I) are obtained in virtually quantitative yield and in very high purity. The process according to the invention is (from a process engineering perspective) very simple and suitable for performing on a large scale.

Overall, the process according to the invention, and also the process for producing glufosinate described below, form fewer undesired secondary components so that these processes are more efficient and more energy-saving.

The respective alkyl radicals of the radicals $R^1$ and $R^2$ may have a straight-chain or branched-chain (branched) carbon skeleton.

The expression "$(C_1-C_4)$-alkyl", by way of example, is a brief notation for an alkyl radical having 1 to 4 carbon atoms, i.e. encompasses the radicals methyl, ethyl, 1-propyl, 2-propyl, 1-butyl, 2-butyl, 2-methylpropyl or tert-butyl. General alkyl radicals having a larger specified range of carbon atoms, for example "$(C_1-C_6)$-alkyl", correspondingly also encompass straight-chain or branched alkyl radicals having a greater number of carbon atoms, i.e. also the alkyl radicals having 5 and 6 carbon atoms.

"Halogen" preferably refers to the group consisting of fluorine, chlorine, bromine and iodine. Haloalkyl, haloaryl, haloaralkyl and halocycloalkyl respectively refer to alkyl, aryl, aralkyl and cycloalkyl partially or completely substituted by identical or different halogen atoms, preferably from the group fluorine, chlorine and bromine, in particular from the group fluorine and chlorine. Thus haloalkyl encompasses for example monohaloalkyl (=monohalogenalkyl), dihaloalkyl (=dihalogenalkyl), trihaloalkyl (=trihalogenalkyl) or else perhaloalkyl, for example $CF_3$, $CHF_2$, $CH_2F$, $CF_3CF_2$, $CH_2FCHCl$, $CCl_3$, $CHCl_2$, $CH_2CH_2Cl$. The same applies for the other halogen-substituted radicals.

The process according to the invention preferably relates to producing phosphinates (phosphonous acid monoesters) of formula (I)
where in each case
$R^1$ represents $(C_1-C_6)$-alkyl, $(C_1-C_6)$-haloalkyl, $(C_6-C_8)$-aryl, $(C_6-C_8)$-haloaryl, $(C_7-C_{10})$-aralkyl, $(C_7-C_{10})$-haloaralkyl, $(C_5-C_8)$-cycloalkyl or $(C_5-C_8)$-halocycloalkyl, and
$R^2$ represents $(C_3-C_8)$-alkyl, $(C_3-C_8)$-haloalkyl, $(C_6-C_8)$-aryl, $(C_6-C_8)$-haloaryl, $(C_7-C_{10})$-aralkyl, $(C_7-C_{10})$-haloaralkyl, $(C_5-C_8)$-cycloalkyl or $(C_5-C_8)$-halocycloalkyl.

The process according to the invention preferably relates to producing phosphinates (phosphonous acid monoesters) of formula (I)
where in each case
$R^1$ represents $(C_1-C_4)$-alkyl, $(C_1-C_4)$-haloalkyl or $(C_6-C_8)$-aryl, preferably methyl or ethyl,
and
$R^2$ represents $(C_3-C_6)$-alkyl or $(C_3-C_6)$-haloalkyl, preferably $(C_3-C_6)$-alkyl, preference among these in turn being given to $C_4$-alkyl or $C_5$-alkyl.

The process according to the invention relates in particular to producing certain alkyl phosphinates (alkylphosphonous acid monoesters) of formula (I), in which particularly preferably in formula (I)
$R^1$ represents methyl, and
$R^2$ represents $(C_3-C_6)$-alkyl, particular preference in turn being given to $(C_4-C_5)$-alkyl.

The implementations which follow and the embodiments of the process according to the invention characterized as preferable/particularly preferable apply in particular for the reaction of a compound of formula (I), in which $R^1$ represents methyl and $R^2$ represents $(C_3-C_6)$-alkyl.

An advantageous process according to the invention is characterized in that the total amount of water used is at least 0.8 molar equivalents, preferably at least 0.9 molar equivalents, more preferably at least 0.95 molar equivalents, based in each case on the total amount of compounds of formula (II) used.

A preferred process according to the invention is characterized in that the total amount of water used is 1 to 5 molar equivalents, based on the total amount of compounds of formula (II) used.

A particularly preferred process according to the invention is characterized in that the total amount of water used is 1 to 3 molar equivalents, especially preferably 1 to 2 molar equivalents, based in each case on the total amount of compounds of formula (II) used.

A preferred process according to the invention is characterized in that the total amount of compounds of formula (III) used is 1 to 25 molar equivalents, preferably 2 to 20 molar equivalents, based in each case on the total amount of compounds of formula (II) used.

A particularly preferred process according to the invention is characterized in that the total amount of compounds of formula (III) used is 3 to 15 molar equivalents, preferably 4 to 12 molar equivalents, preferably 5 to 10 molar equivalents, based in each case on the total amount of compounds of formula (II) used.

A preferably recovered excess of the compound (III) may subsequently be reused in the same reaction without further purification.

In a preferred configuration in the process according to the invention, preference is given to using initially a portion of the overall total amount of alcohols of formula (III) used in the reaction. By way of preference, initially a proportion of 20 to 80% by weight, preferably a proportion of 30 to 70% by weight, more preferably a proportion of 40 to 60% by weight of the overall total amount of the alcohols of formula (III) used is mixed and reacted with the compounds of formula (II), water and acidic catalyst, before the residual amount of the overall total amount of the alcohols of formula (III) used is added to the resulting reaction mixture.

A preferred process according to the invention is characterized in that the pKa of the acidic catalyst under standard conditions (273.15 K and 100 kPa) is less than 3, preferably less than 2, and preferably less than 1.

In one process according to the invention, preference is given to acidic catalysts selected from $H_3PO_3$, $H_2SO_4$, HCl, HBr, $HClO_4$, dichloroacetic acid, trichloroacetic acid, trifluoroacetic acid, methanesulphonic acid, trifluoromethanesulphonic acid, benzenesulphonic acid and p-toluenesulphonic acid.

In one process according to the invention, preference is given to acidic heterogeneous (solid) catalysts selected from acidic ion exchangers, acidic polysiloxanes and acidic zeolites.

A preferred process according to the invention, therefore, is characterized in that one or the acidic catalyst is selected from the group consisting of $H_3PO_3$, $H_2SO_4$, HCl, HBr, $HClO_4$, dichloroacetic acid, trichloroacetic acid, trifluoroacetic acid, methanesulphonic acid, trifluoromethanesulphonic acid, benzenesulphonic acid, p-toluenesulphonic acid, acidic ion exchangers, acidic polysiloxanes and acidic zeolites.

A particularly preferred process according to the invention is characterized in that the pKa of the acidic catalyst under standard conditions (273.15 K and 100 kPa) is less than 0 (zero), and preferably less than −1.

Particular preference is given to acidic catalysts selected from $H_2SO_4$, HCl, methanesulphonic acid, trifluoromethanesulphonic acid and p-toluenesulphonic acid.

Particularly preferred acidic heterogeneous (solid) catalysts are those having sulphonic acid groups, i.e. —$SO_3H$ groups.

The overall amount used (total amount) of the acidic catalyst(s) in the process according to the invention is not critical for carrying out the process according to the invention, being preferably 0.1 to 10% by weight, preferably 0.5 to 5% by weight, based in each case on the overall amount used (total amount) of the compounds of formula (II).

A particular advantage and a particularly preferred configuration of the process according to the invention are characterized in that the reaction is carried out as a one-pot reaction, i.e. reaction of compounds (II) and (III) to give compound (I) is particularly preferably carried out in accordance with the invention without isolation of intermediates.

The process according to the invention is preferably carried out such that the reaction is carried out at a temperature in the range from 30 to 140° C., preferably at a temperature in the range from 40 to 130° C., more preferably at a temperature in the range from 50 to 120° C. and particularly preferably at a temperature in the range from 60 to 110° C.

The process according to the invention enables the production of the phosphinates (phosphonous acid monoesters) of formula (I) under mild reaction conditions and in a manner that is simpler to carry out in terms of process/plant engineering. The phosphinates (phosphonous acid monoesters) of formula (I) can therefore be obtained more easily in process engineering terms, in better yields and in high purity.

The purity of the desired products of formula (I) after purification, for example, after purification by distillation, is regularly greater than 95%.

The process according to the invention is therefore particularly suitable for carrying out on an industrial scale, i.e. the process according to the invention is preferably carried out in a manner in which at least an amount of 100 kg of compounds of formula (II) is used in the process according to the invention, preferably at least an amount of 250 kg of compounds of formula (II), more preferably at least an amount of 500 kg of compounds of formula (II).

The phosphinates (phosphonous acid monoesters) of formula (I) formed may be used as starting materials for the synthesis of phosphorus-containing amino acids such as glufosinate and glufosinate salts.

Preferred configurations of the process according to the invention for producing the compounds of formula (I) by reacting a compound of formula (II) with the alcohol of formula (III) are characterized in that
the total amount of water used is 1 to 3 molar equivalents, based on the total amount of compounds of formula (II) used,
and
the total amount of compounds of formula (III) used is 2 to 20 molar equivalents, more preferably the total amount of compounds of formula (III) used is 3 to 15 molar equivalents, based in each case on the total amount of compounds of formula (II) used.

Further preferred configurations of the process according to the invention for producing the compounds of formula (I) by reacting a compound of formula (II) with the alcohol of formula (III) are characterized in that
the total amount of water used is 1 to 2 molar equivalents, based on the total amount of compounds of formula (II) used,
and
the total amount of compounds of formula (III) used is 4 to 12 molar equivalents, more preferably the total amount of compounds of formula (III) used is 5 to 10 molar equivalents, based in each case on the total amount of compounds of formula (II) used.

Particularly preferred configurations of the process according to the invention for producing the compounds of formula (I) by reacting a compound of formula (II) with the alcohol of formula (III) are characterized in that
the total amount of water used is 1 to 3 molar equivalents, based on the total amount of compounds of formula (II) used,
the total amount of compounds of formula (III) used is 2 to 20 molar equivalents, more preferably the total amount of compounds of formula (III) used is 3 to 15 molar equivalents, based in each case on the total amount of compounds of formula (II) used,
the acidic catalyst(s) are selected from the group consisting of $H_2SO_4$, HCl, methanesulphonic acid, trifluoromethanesulphonic acid, p-toluenesulphonic acid and acidic heterogeneous (solid) catalysts having sulphonic acid groups, i.e. —$SO_3H$ groups,
the reaction is carried out at a temperature in the range from 30 to 140° C., preferably at a temperature in the range from 40 to 130° C.,
and the overall amount used (total amount) of the acidic catalyst(s) is preferably 0.1 to 10% by weight, preferably 0.5 to 5% by weight, based in each case on the overall amount used (total amount) of compounds of formula (II).

Particularly preferred configurations of the process according to the invention for producing the compounds of formula (I) by reacting a compound of formula (II) with the alcohol of formula (III) are characterized in that
the total amount of water used is 1 to 2 molar equivalents, based on the total amount of compounds of formula (II) used,
the total amount of compounds of formula (III) used is 3 to 15 molar equivalents, more preferably the total amount of compounds of formula (III) used is 4 to 12 molar equivalents, based in each case on the total amount of compounds of formula (II) used,
the acidic catalyst(s) are selected from the group consisting of $H_2SO_4$, HCl, methanesulphonic acid, trifluoromethanesulphonic acid, p-toluenesulphonic acid and acidic heterogeneous (solid) catalysts having sulphonic acid groups, i.e. —$SO_3H$ groups,
the reaction is carried out at a temperature in the range from 50 to 120° C., preferably at a temperature in the range from 60 to 110° C.,
and
the overall amount used (total amount) of the acidic catalyst(s) is 0.5 to 5% by weight, based on the overall amount used (total amount) of compounds of formula (II).

The process according to the invention may be carried out either in a discontinuous process regime (for example in a semibatch mode of operation) or else in a continuous process regime (for example in a continuously operated stirred tank).

The process according to the invention is preferably carried out under inertization, preferably in a protective gas atmosphere. Preferred protective gases in this case are nitrogen/argon.

It is further possible to carry out the process according to the invention under superatmospheric pressure or under reduced pressure.

The process according to the invention may be carried out in an inert diluent or diluent-free.

If the process according to the invention is carried out in an inert diluent, i.e. stable under the reaction conditions, the diluent is preferably selected from the group consisting of hydrocarbons (preferred in this case are alkanes and aromatic hydrocarbons), halogenated hydrocarbons (preferred in this case are haloalkanes and halogenated aromatic hydrocarbons), ethers (preferred in this case are cyclic ethers, alkyl alkyl ethers and aryl alkyl ethers), carboxylic acid esters (preferred in this case are alkyl alkyl esters and aryl alkyl esters) and carboxamides, and mixtures thereof.

Usable optional diluents in the process according to the invention are inert organic solvents such as heptane, toluene, xylene, ethylbenzene, chlorobenzene, dichlorobenzene, anisole, dimethyl formamide (DMF), dimethylacetamide, N-methyl-2-pyrrolidone (NMP) or mixtures of these organic solvents.

Preferred diluents in this case are heptane, toluene, xylene, ethylbenzene, cumene, chlorobenzene, dichlorobenzene, anisole and mixtures thereof.

More preferably, the diluent forms an azeotropic mixture with the alcohol(s) methanol and/or ethanol resulting from the residues $R^3$ or $R^4$ of the compound of formula (II) in the process according to the invention, which can preferably be removed from the reaction mixture by distillation, i.e. can be distilled off. Preferred diluents in this regard are aromatic hydrocarbons, preference in turn being given to alkylbenzenes such as toluene, xylene and/or ethylbenzene.

In a preferred configuration, the process according to the invention is carried out without addition of a diluent.

Glufosinate salts in the context of the present invention are preferably ammonium salts, phosphonium salts, sulfonium salts, alkali metal salts and alkaline earth metal salts of glufosinate.

Especially preferred in the context of the present invention are glufosinate, glufosinate sodium and glufosinate ammonium.

Finally, the present invention also relates to the use of a compound of formula (I), produced in accordance with a process according to the invention, as defined above, for producing biologically active substances which may be used in the pharmaceutical or agrochemical sector, preferably for producing phosphorus-containing amino acids, particularly for producing glufosinate or glufosinate salts, in this case particularly glufosinate, glufosinate sodium or glufosinate ammonium.

The process for producing glufosinate and/or glufosinate salts may be effected in similar fashion as described for example in U.S. Pat. No. 4,521,348.

The examples which follow elucidate the present invention.

EXAMPLES

All data are based on weight unless otherwise stated.

Example 1

1-Butyl methylphosphinate (methanephosphonous acid mono-n-butyl ester)

38.45 g (0.2684 mol) of diethyl methylphosphonite (purity 95%) and 1.5 g of Amberlyst® 15 (strongly acidic catalyst, synthetic ion exchange resin) in 200 ml of toluene were initially charged in a stirred flask under an argon atmosphere. 4.95 g (0.275 mol) of water and 50 g (0.675 mol) of 1-butanol were added while stirring. Subsequently, the mixture was stirred at 50° C. for 30 min and then heated to reflux (initially ca. 83° C.).

Low boiling components (ethanol and toluene) were then distilled off via a distillation attachment with a short Vigreux column. After 4 hours another 50 g (0.675 mol) of 1-butanol were added and further low boiling components were distilled off. Finally, at 140° C. at the bottom/113° C. at the top, a mixture of 37% 1-butanol and 63% toluene (GC analysis) was removed.

After cooling and removal of the acidic catalyst, 64.3 g remained of a mixture of 55.6% 1-butyl methylphosphinate, 41.3% 1-butanol and 3.1% toluene (GC analysis against standard), corresponding to a yield of 35.75 g (0.263 mol) =97.9% of theory.

By means of a fractionated fine distillation under reduced pressure, 1-butyl methylphosphinate was obtained at a purity of 98.5%.

Analysis: $^{31}$P-NMR (CDCl$_3$)
1-butyl methylphosphinate 33.9 ppm
diethyl methylphosphonite 177.8 ppm Example 2

1-Pentyl methylphosphinate (methanephosphonous acid mono-n-pentyl ester)

To 20 g (0.145 mol) of diethyl methylphosphonite (purity 99%) were added 2.62 g (0.145 mol) of water and 64.1 g (0.727 mol) of 1-pentanol and the mixture was reacted in the presence of 0.1 g of 96% sulphuric acid without additional solvent, wherein the mixture was stirred at the start at 50° C. for 30 minutes, and then the internal temperature was increased gradually over 3 hours up to the reflux temperature of 1-pentanol by the end. At the same time, low boiling components were distilled off, at the end only 1-pentanol (GC analysis), which was mostly distilled off.

According to analysis by GC, the resulting reaction mixture no longer contained reactant.

After fine distillation under reduced pressure, 21.8 g (0.139 mol) of 1-pentyl methylphosphinate (purity 96%) were obtained from the crude product, corresponding to a yield of 95.8% of theory.

Analysis: $^{31}$P-NMR (CDCl$_3$): 1-pentyl methylphosphinate 34.11 ppm

Example 3

1-Butyl phenylphosphinate (phenylphosphonous acid mono-n-butyl ester)

To 5.0 g (24.7 mmol) of diethyl phenylphosphonite (purity 98%) under argon were added 9.72 g (131.17 mmol) of 1-butanol, 0.445 g (24.7 mmol) of water and 0.3 g of Amberlyst® 15 (strongly acidic catalyst, synthetic ion exchange resin) at 20° C. without additional diluent and the mixture was heated to reflux. Low boiling components were then distilled off via a distillation attachment with a short Vigreux column up to a bottom temperature of 117-120° C. A further 8.1 g (109.31 mmol) of 1-butanol were then added and low boiling components further distilled off at a bottom temperature of about 120° C. The overall reaction lasted in total about 5.5 hours. The profile was monitored by GC analysis. 7.95 g of crude product remained at the end (according to $^{1}$H-NMR 58.3%, the residue was 1-butanol). This corresponded to a yield of 94.6% of theory.

Pure 1-butyl phenylphosphinate could be obtained via a fine distillation under reduced pressure.

Analysis: $^{31}$P-NMR (CDCl$_3$)
1-butyl phenylphosphinate 25.1 ppm
diethyl phenylphosphonite 151.2 ppm

Example 4

2-Methylpropyl phenylphosphinate
(phenylphosphonous acid mono-2-methylpropyl ester)

Analogously to Example 2 above, diethyl phenylphosponite (purity 98%) was reacted with water (1 molar equivalent) and isobutanol (8 molar equivalents) in the presence of a catalytic amount of concentrated sulphuric acid (2 mol %, based on the amount of diethyl phenylphosphonite used).

2-Methylpropyl phenylphosphinate was obtained in a yield of 95.0% of theory, which had a purity of 98% after fine distillation.

Analysis: $^{31}$P-NMR (CDCl$_3$): 2-methylpropyl phenylphosphinate 25.4 ppm

Example 5

2-Methylpropyl phenylphosphinate
(phenylphosphonous acid mono-2-methylpropyl ester)

Analogously to Example 3 above, diethyl phenylphosponite (purity 98%) was reacted with water (1 molar equivalent) and isobutanol (20 molar equivalents, which were added in two roughly equal portions) in the presence of a catalytic amount of methane sulphonic acid (1% by weight, based on the amount of diethyl phenylphosphonite used).

2-Methylpropyl phenylphosphinate was obtained in a yield of 97.0% of theory, which had a purity of 98.5% after fine distillation.

Analysis: $^{31}$P-NMR (CDCl$_3$): 2-methylpropyl phenylphosphinate 25.3 ppm

The invention claimed is:

1. A process for producing a compound of formula (I)

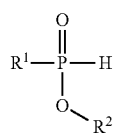
(I)

comprising reacting a compound of formula (II)

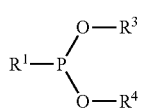
(II)

with a compound of formula (III)

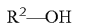
(III)

wherein in each case:
R$^1$ represents (C$_1$-C$_{12}$)-alkyl, (C$_1$-C$_{12}$)-haloalkyl, (C$_6$-C$_{10}$)-aryl, (C$_6$-C$_{10}$)-haloaryl, (C$_7$-C$_{10}$)-aralkyl, (C$_7$-C$_{10}$)-haloaralkyl, (C$_4$-C$_{10}$)-cycloalkyl or (C$_4$-C$_{10}$)-halocycloalkyl,
R$^2$ represents (C$_3$-C$_{12}$)-alkyl, (C$_3$-C$_{12}$)-haloalkyl, (C$_6$-C$_{10}$)-aryl, (C$_6$-C$_{10}$)-haloaryl, (C$_7$-C$_{10}$)-aralkyl, (C$_7$-C$_{10}$)-haloaralkyl, (C$_4$-C$_{10}$)-cycloalkyl or (C$_4$-C$_{10}$)-halocycloalkyl,
R$^3$ and R$^4$ each independently of one another represent methyl or ethyl,
in the presence of an acidic catalyst and in the presence of water.

2. The process according to claim 1, wherein the total amount of water used is at least 0.8 molar equivalents, based on the total amount of compounds of formula (II) used.

3. The process according to claim 1, wherein the total amount of water used is 1 to 5 molar equivalents, based on the total amount of compounds of formula(II) used.

4. The process according to claim 1, wherein the total amount of water used is 1 to 3 molar equivalents, based on the total amount of compounds of formula (II) used.

5. The process according to claim 1, wherein the total amount of water used is 1 to 2 molar equivalents, based on the total amount of compounds of formula (II) used.

6. The process according to claim 1, wherein the total amount of compounds of formula (III) used is 1 to 25 molar equivalents, based on the total amount of compounds of formula (II) used.

7. The process according to claim 1, wherein the total amount of compounds of formula (III) used is 3 to 15 molar equivalents, based in each case on the total amount of compounds of formula (II) used.

8. The process according to claim 1, wherein the pKa of the acidic catalyst under standard conditions is less than 3.

9. The process according to claim 1, wherein the acidic catalyst is selected from the group consisting of H$_3$PO$_3$, H$_2$SO$_4$, HCl, HBr, HClO$_4$, dichloroacetic acid, trichloroacetic acid, trifluoroacetic acid, methanesulphonic acid, trifluoromethanesulphonic acid, benzenesulphonic acid, p-toluenesulphonic acid, acidic ion exchangers, acidic polysiloxanes and acidic zeolites.

10. The process according to claim 1, wherein the reaction is carried out as a one-pot reaction.

11. The process according to claim 1, wherein the reaction is carried out at a temperature in a range from 30 to 140° C.

12. The process according to claim 1, wherein the reaction is carried out in an inert diluent or diluent-free.

13. The process according to claim 1, wherein
R$^1$ represents (C$_1$-C$_6$)-alkyl, (C$_1$-C$_6$)-haloalkyl, (C$_6$-C$_8$-aryl, (C$_6$-C$_8$-haloaryl, (C$_7$-C$_{10}$)-aralkyl, (C$_7$-C$_{10}$)-haloaralkyl, (C$_5$-C$_8$-cycloalkyl or (C$_5$-C$_8$-halocycloalkyl, and
R$^2$ represents (C$_3$-C$_8$)-alkyl, (C$_3$-C$_8$)-haloalkyl, (C$_6$-C$_8$-aryl, (C$_6$-C$_8$-haloaryl, (C$_7$-C$_{10}$)-aralkyl, (C$_7$-C$_{10}$)-haloaralkyl, (C$_5$-C$_8$-cycloalkyl or (C$_5$-C$_8$-halocycloalkyl.

14. The process according to claim 1, wherein $R^1$ represents $(C_1-C_4)$-alkyl, $(C_1-C_4)$-haloalkyl or $(C_6-C_8)$-aryl $R^2$ represents $(C_3-C_6)$-alkyl or $(C_3-C_6)$-haloalkyl.

15. The process according to claim 1, wherein $R^1$ represents methyl or ethyl, $R^2$ represents $C_4$-alkyl or $C_5$-alkyl.

16. The process according to claim 1, wherein the total amount of water used is at least 0.95 molar equivalents, based on the total amount of compounds of formula (II) used.

17. The process according to claim 1, wherein the total amount of compounds of formula (III) used is 5 to 10 molar equivalents, based on the total amount of compounds of formula (II) used.

18. The process according to claim 1, wherein the pKa of the acidic catalyst under standard conditions is less than 2.

19. The process according to claim 1, wherein the reaction is carried out at a temperature in a range from 50 to 120° C.

* * * * *